(12) United States Patent
Neeper et al.

(10) Patent No.: US 7,421,831 B2
(45) Date of Patent: Sep. 9, 2008

(54) SYSTEM AND METHOD FOR SIMULTANEOUS CAPPING/DE-CAPPING OF STORAGE CONTAINERS IN AN ARRAY

(75) Inventors: Robert K. Neeper, Ramona, CA (US); John Bridwell, San Diego, CA (US)

(73) Assignee: Nexus Biosystems, Inc., Poway, CA (US)

( * ) Notice: Subject to any disclaimer, the term of this patent is extended or adjusted under 35 U.S.C. 154(b) by 0 days.

(21) Appl. No.: 11/555,621

(22) Filed: Nov. 1, 2006

(65) Prior Publication Data

US 2007/0095024 A1 May 3, 2007

Related U.S. Application Data

(60) Provisional application No. 60/732,032, filed on Nov. 1, 2005.

(51) Int. Cl.
*B65B 1/04* (2006.01)
*B65B 43/20* (2006.01)
*B67B 7/62* (2006.01)

(52) U.S. Cl. .......................... 53/381.4; 53/321; 53/328; 81/3.37

(58) Field of Classification Search ............ 53/287, 53/299, 319, 321, 328, 381.4, 485, 492; 81/3.15, 81/3.2, 3.27, 3.37
See application file for complete search history.

(56) References Cited

U.S. PATENT DOCUMENTS

| 1,451,351 | A | * | 4/1923 | Van Doren | 53/299 |
|---|---|---|---|---|---|
| 2,828,593 | A | * | 4/1958 | Colgren et al. | 53/76 |
| 3,520,102 | A | * | 7/1970 | Henrion | 53/77 |
| 3,589,103 | A | * | 6/1971 | Calvillo et al. | 53/381.4 |
| 4,070,854 | A | * | 1/1978 | Marino | 53/381.4 |
| 4,199,050 | A | | 4/1980 | Moller | |
| 4,265,071 | A | * | 5/1981 | Smith et al. | 53/492 |
| 4,338,764 | A | * | 7/1982 | Percarpio | 53/432 |
| 4,522,089 | A | * | 6/1985 | Alvi | 81/3.42 |
| 4,850,470 | A | * | 7/1989 | Ferkany | 198/345.3 |
| 5,083,416 | A | * | 1/1992 | Schneider et al. | 53/489 |
| 5,519,984 | A | * | 5/1996 | Beussink et al. | 53/489 |
| 5,778,740 | A | | 7/1998 | Tye | |
| 6,205,743 | B1 | | 3/2001 | Castellari | |
| 6,253,807 | B1 | | 7/2001 | Jones | |

(Continued)

OTHER PUBLICATIONS

International Search Report and Written Opinion in PCT/US06/33915 dated Sep. 28, 2007.

*Primary Examiner*—Paul R Durand
(74) *Attorney, Agent, or Firm*—Procopio, Cory, Hargreaves & Savitch, LLP (57) ABSTRACT

The system for removing or replacing caps for vials in a fixed array includes a removable cartridge with a plurality of sets of gripper plates corresponding to the number of columns in the array. Each plate has a plurality of gripper arms corresponding to the number of rows in the array. The gripper arms have hooked ends which are oriented in opposite directions in each set of plates. Relative positioning of the gripper arms is varied by one or more rotating cams, which cause the gripper arms on one plate of each set to move relative to the gripper arms of the other plate(s) of the set, varying the combined width and/or relative angle of the gripper arms to manipulate a cap inserted into the end of each vial. The plurality of plate sets and gripper arms allow all vials in the array to be capped or de-capped simultaneously.

18 Claims, 6 Drawing Sheets

U.S. PATENT DOCUMENTS

| | | |
|---|---|---|
| 6,477,919 B1 | 11/2002 | Thomas et al. |
| 6,543,203 B2 | 4/2003 | Thompson et al. |
| 6,874,389 B1 | 4/2005 | Thornton |
| 6,875,205 B2 | 4/2005 | Leinsing |
| 6,896,848 B1 | 5/2005 | Warhurst et al. |
| 7,152,504 B2 * | 12/2006 | Itoh ............... 81/3.2 |

* cited by examiner

SYSTEM AND METHOD FOR SIMULTANEOUS CAPPING/DE-CAPPING OF STORAGE CONTAINERS IN AN ARRAY

RELATED APPLICATIONS

This application claims the priority of U.S. Provisional Application No. 60/732,032, filed Nov. 1, 2005, which is incorporated herein by reference in its entirety.

FIELD OF THE INVENTION

The invention generally relates to a system and method for the removal and installation of caps on a container within an array, and more particularly to an automated system for simultaneously capping and de-capping multiple vials in a tray.

BACKGROUND OF THE INVENTION

In the search for new compounds, especially for the pharmaceutical industry, combinatorial methods demand creation and testing of a significant number of compounds.

Using modern techniques and tools, only small aliquots of chemicals are required for testing, therefore small storage containers, such as compound storage vials, can be used to collect and store the chemical compounds. The vials are normally kept in a tray specially designed for the storage and transportation of the vials. The trays come in varying sizes and hold a varying quantity of vials. A typical tray may hold an array, 8×12, of 96 vials. The vial size will depend on the required aliquot. Once all of the vials in the tray are filled with chemicals, they may be stacked one upon another and placed in a storage area. Dozens of the 96 vial trays may be used for collecting the chemical compounds from a single experiment and may need to be kept for future evaluations. Trays that contain hundreds of vials which hold only microliters of solution are also available as well as trays that hold only a few vials but contain several milliliters.

For storage and transportation of the trays, and to protect the chemical compounds from contamination or spillage, the vials are typically capped. The caps are generally made from a non-reactive, compliant plastic material. The caps are pressed into the top of the vial or in some cases, onto and over the top of the vial. The caps preferably form an air tight seal that protects the contents of the vials from the external environment and eliminates loss of the chemical compound. The caps also allow the trays to be stacked without compromising the chemical compounds within the vials.

In order to sample the chemical compound in each of the vials or in one vial, the caps must first be removed, the contents tested, and the caps replaced each time. There are tools commercially available, such as REMP AG's 'Automated Capper Decapper 96 (ACD96), (Ch-3672 Oberdiessbach, Switzerland), that can de-cap and re-cap 96 tubes at one time. Once the tubes are de-capped, the tray with the tubes is removed from the tool so the required analysis may be performed. Once the analysis is complete, the tray is returned to the de-capping/re-capping tool so the tubes can be re-capped. To avoid cross contamination of the sample from placing a cap on the wrong tube, either new caps must be used in the recapping process or the de-capping/re-capping tool must sit idle and not be used so that the caps that were removed are held in the system in the exact position so that they will be replaced on the same container that they were removed from. This is not practical due to the expense of new caps every time the samples are tested or tying up of the de-capping/re-capping tool while the analysis is performed.

Another method of sealing vials is to use a cap mat which is a solid plastic mat with cap protrusions for 96 vials formed as part of the mat on one side. The mat is placed on top of the 96 vials, placed into a sealer, and all 96 vials are sealed at one time and are connected by the mat. This technology is offered by REMP AG as well as Matrix Technologies Corporation (Hudson, N.H.) using their Matrix SuperSealer® Automatic Cap Mat Sealer. A disadvantage of cap mats is that one or more selected vials may not be removed from the holder after they have been sealed with the cap mat.

A bottle cap remover has been described in U.S. Pat. No. 5,778,740 (Tye). Here, a cap placed on the top, external surface of a bottle and is removed by a hook-shaped member. This tool requires that the cap fit over the outside of the upper edge of the bottle. Another de-capping tool described in U.S. Pat. No. 6,477,919 (Thomas et al.) removes caps from bottles or vials. Here, too, the cap must fit over the outside of the upper edge of the bottle. Both of these patents describe a tool only for the removal of a cap, and not for the replacement or storage of a cap.

In addition to the storage of chemical compounds, other fields of research have needs for storage of small amounts of materials that are well-suited for the types of storage that are described above. For example, biology and medical researchers often have the need for long term storage of small volumes of biological materials such as bacterial, fungal, viral, ELISA or PCR samples, to name a few. Many research institutions amass large libraries of samples and controls and make such materials available to other researchers. Forensic laboratories, and particularly law enforcement agencies, have the need to retain evidence for long periods of times, which evidence often includes biological specimens, such as tissue, blood or other specimens for DNA testing. Industrial applications for such capabilities include the retention of standards for quality control and samples for batch tracking. There is a wide range of applications across virtually every scientific discipline that would benefit from the ability to store large quantities of small samples in arrays of vials.

There is a need for a tool that will allow the capping/de-capping of an array of sample storage vials while maintaining the original caps in the exact positions from which they were removed, and that will allow for numerous trays to be continually processed while maintaining tray identity that matches the caps. The present invention is directed to this need.

SUMMARY OF THE INVENTION

It is an advantage of the present invention to provide an apparatus and method for the automatic removal and replacement of a plurality of caps into a plurality of storage containers such as vials.

It is another advantage of the present invention to provide a removable cartridge in an automated capper/de-capper system that allows the system to be used on other trays of vials so that the system need not sit idle until testing is completed on a first array of vials.

The capper/de-capper system for removing or replacing caps for vials in a fixed array includes a removable cartridge with a plurality of sets of gripper plates corresponding to the number of columns in the array. Each set can have either two or three plates, and each plate has a plurality of gripper arms corresponding to the number of rows in the array. The gripper arms have hooked ends which are oriented in opposite directions in each pair of plates. Relative positioning of the gripper arms, is varied by one or more rotating cams, which cause the gripper arms on one or two plates of each set to move relative to the gripper arms of another plate of the set, varying the combined width and/or relative angle of the gripper arms to manipulate a cap that fits into the end of each vial. The plurality of plate sets and gripper arms allow all vials in the array to be capped or de-capped simultaneously.

In the illustrative embodiment, the cartridge is dimensioned for handling of 96 vials in an 8×12 array. Cartridges with different dimensions may be provided to accommodate more or fewer vial quantities in different arrays.

The removable cartridge of the present invention includes a frame surrounding a plurality of sets of elongated plates, each plate set corresponding to either one row or one column of vials in the array. In the illustrative embodiment, 8 pairs of plates are used for the 96 vial container. Each set of plates has a plurality of gripper arms extending downward from the bottom of the plate. The gripper arms are "L"- or "J"-shaped hooks that are dimensioned to fit within the top recess of a cap. In the 96 vial container, each plate will have 12 gripper arms. For a plate pair, two corresponding gripper arms are oriented in opposite directions so that their hooked portions are pointed away from each other. For a three plate set, where two plates move and a third plate is relatively stationary, the hooked portions of the moving plates will generally point away from the hooked portions of the stationary plate.

Adjacent plate sets are separated from each other by a spacer that corresponds to the spacing between the vials so that, when the cartridge is aligned with the array of vials, there will be a pair of gripper arms positioned over each vial. The spacer is generally cylindrical and is supported in place by two or more rods that extend through openings formed in each of the plates.

In one embodiment, a single cylindrical cam shaft with a cam disposed near either end drives movement of a first plate of each pair of plates. The cam shaft extends rotatably through a closely fitted circular opening at the lengthwise center of the first plate. The cams, which are identical and generally triangular in shape, move within corresponding cam races that are disposed on the frame to cause the cam shaft to describe a parallelogram that is horizontal and slightly skewed vertically. The second plate is stationary relative to the frame, held in place by static locating rods extending through an opening at each end of the plate and supported at each end of the rod by the frame. The cam shaft passes through a large opening at the lengthwise center of the second plate that permits the cam shaft to move freely without contacting any edges of the center opening. The static locating rods extend through openings near the ends of the first plate that are dimensioned to permit the first plate to move horizontally and vertically through the desired range. Stops disposed on the frame serve to limit the first plates' vertical travel and force the first plate to be level at this extreme of travel, eliminating the need for multiple cams. Preferably, the openings at the ends of the first plate serve as stops to limit vertical travel to an appropriate range.

As the cam shaft rotates it causes the first plate to move, varying the combined width of the corresponding gripper arms to expand to grip or contract to release the sidewalls of the cap recess, and to vary the angle of the corresponding gripper arms to lift and stretch the cap for removal or replacement.

In another embodiment, motion of each pair of plates is controlled by one or more cam-shaped rods that extend through generally rectangular openings in the plates. The cam-shaped rods rotate within the openings to vary the relative position and configuration of the gripper arms. A beveled corner within each opening acts as a cam follower for producing up or down movement when contacted by the major axis of the cam. The cam also produces relative sideways movement of the plates when the major axis of the cam is aligned generally horizontally. Typically, a cartridge will have two or more cams that are operably linked so that rotation of the cams is coordinated. The linkage is supported by the frame and provides connection to a drive mechanism that rotates the cam.

The cartridge is configured for removable insertion into a cartridge holder of a robotic apparatus that is capable of lifting and lowering the vial tray in an aligned relationship with a cartridge holder. The cartridge holder includes means for connecting a drive motor for activating the cams within the cartridge. When de-capping of vials is desired, the caps can be retained within the cartridge that was used to extract them. The cartridge can be removed from the apparatus with the caps in place and stored in a safe location until the vials are to be re-sealed. The correct positioning of the caps is ensured because the caps remain in the same location from which they were removed, thus preventing cross-contamination. The cartridge may include means for identifying the cartridge such as a number or a bar code. This number may correspond to the vial tray and may be manually read or automatically read by the equipment to ensure that the cartridge has been properly matched with the vial tray. The cartridge may include one or more protective covers to facilitate stacking and to prevent contamination of the caps. During the time that materials are being drawn from the de-capped vials, a different cartridge can be inserted into the cartridge holder, allowing operations to be performed on other trays of vials. The apparatus may have a means of clearing the cartridge and disposing of used caps that are no longer needed, and for applying new caps.

BRIEF DESCRIPTION OF THE DRAWINGS

FIGS. 1a and 1b are diagrammatic views of an exemplary capping/de-capping system of the present invention where

FIGS. 4a-4d are side views of the gripper plates and gripper arms for the first embodiment of the cartridge, where FIG. 4c is a side view of the cam gripper plate.

FIGS. 8a-8b are side views of the gripper plates, gripper arms, and cam according to the second embodiment, where

DETAILED DESCRIPTION OF THE PREFERRED EMBODIMENTS

The present invention relates to an automated system for the capping and de-capping of vials and for the storage of the removed caps such that cross contamination will not easily occur and costs are reduced by enabling reuse of the original caps. The capper/de-capper system includes a cam operator, a removable cartridge that is used to remove, replace, and temporarily store vial caps for an array of vials, a cartridge elevator and a conveyor driver. The system is preferably computer controlled.

Unless otherwise indicated, the invention is not intended to be limited to any particular materials, dimensions, tray size or number of caps or vials. The use of relative positioning, e.g., up, down, right, left, is not intended to be limiting but is provided for illustrative purposes with reference to the drawings.

The vial caps to which the present invention is directed are of the type that are inserted into the open upper end of a vial and are retained in place by an interference fit between the outer walls of the cap and the inner surface of the upper end of the vial. A flange at the top of the cap contacts the upper lip of the vial to keep the cap from being pushed down into the vial. The cap is generally cylindrical in shape with a recessed center and is formed from a compliant material that allows the cap to produce an airtight seal within the open end of the vial.

Figure 1A:
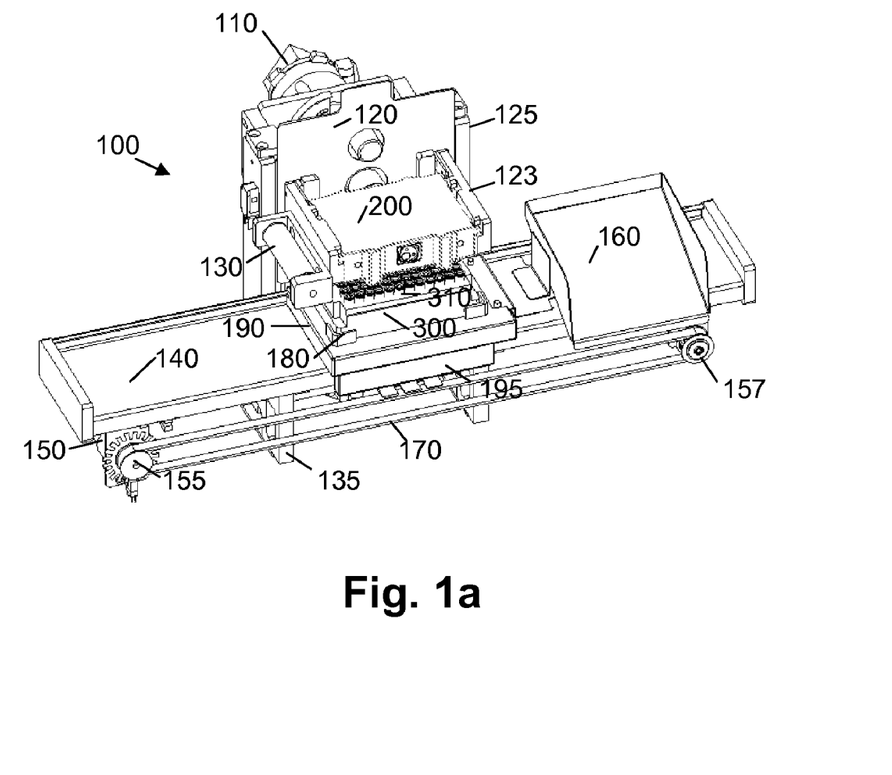
FIG. 1a is a perspective view and FIG. 1b is a front view.
Figure 1B:
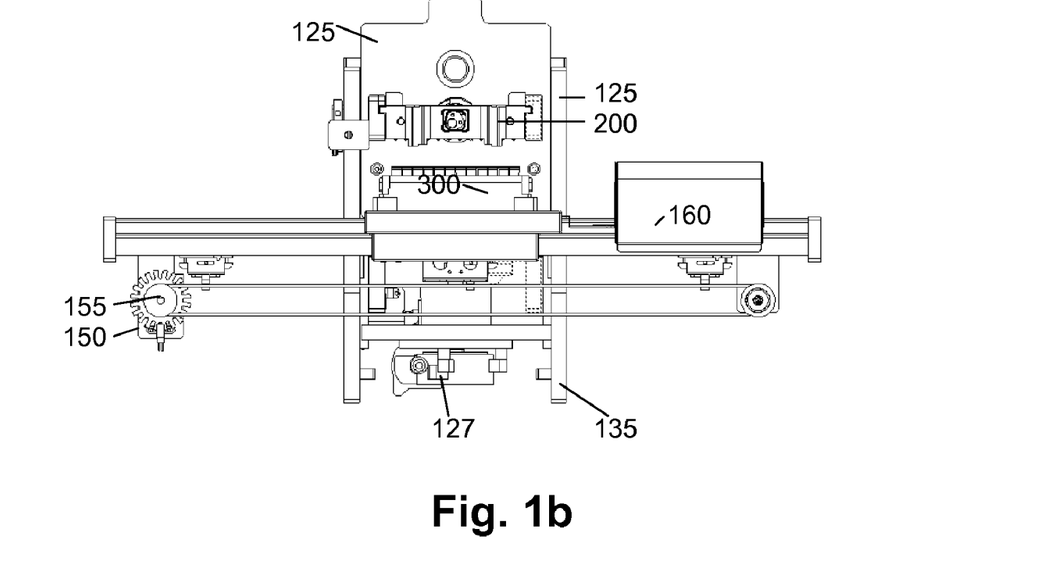

FIGS. 1a and 1b illustrate the operational elements of the capper/de-capper system 100, which includes a conveyor assembly, an elevator assembly 120, a cartridge activator and a cartridge 200, all supported on a stationary base 135. The elevator 120 includes a pair of elevator load arms 123 that extend perpendicular to a vertical elevator wall 122. The load arms 123 are separated by a distance slightly larger than the length of the cartridge 200. In one embodiment, the spacing between the arms 123 may be horizontally adjustable to permit handling of different size cartridges. A recess formed in the inside of each load arm creates a support ledge upon which rests a pair of tabs extending from each end of the cartridge housing, so that the cartridge is supported between the arms. The elevator 120 is slidably supported by, and moves vertically within, elevator tracks 125 attached to and extending from the stationary base 135. An elevator motor 127 drives the elevator movement in response to activation signals, which may include commands from a computer controller (not shown) or the signals may be generated by a user pressing a button or flipping a switch. The elevator motor 127 may be connected to a screw drive, a belt drive, a rack and pinion drive, or any other appropriate drive mechanism. Selection of a suitable drive mechanism will be readily apparent to those of skill in the art.

The conveyor slide 190 moves along a slide plane 140 in a horizontal direction relative to the stationary base 135 and elevator 120. Tray holders 180 extend upward from the top of the conveyor slide 190 to center the tray on the slide and to prevent lateral movement of the tray across the slide. A drive motor 150 disposed on the underside of the slide plane 140 effects movement of the conveyor slide 190 in response to activation signals initiated by an operator or by a computer controller. In the exemplary embodiment, a belt drive mechanism is used, where conveyor slide 190 is linked to drive motor 150 by rotating drive spool 155 and a conveyor drive belt 170. The drive belt 170 loops around a tensioning spool 157 to maintain drive belt tension. The drive belt 170 is attached to the conveyor slide guide 195 to move the conveyor slide 190 laterally when the drive motor 150 turns. Alternative conveyor drive mechanisms are well known in the art and may include a stepper motor with a screw drive, or a rack and pinion drive. Although it is not illustrated, the elevator and at least a portion of the conveyor assembly are partially enclosed within a protective housing formed from Lexan® (polycarbonate), acrylic or a similar polymer, or sheet metal, to minimize the risk of contaminants entering open vials. A loading position, typically at the left side of the system as illustrated in FIGS. 1a and 1b, would be outside of the housing, providing operator access for introducing the tray into the system.

Figure 2:
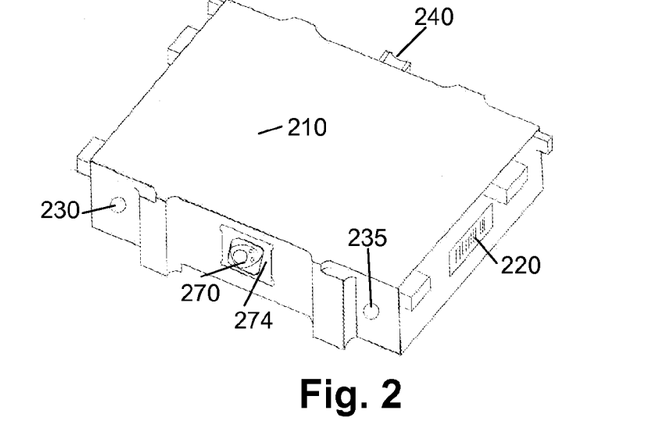
FIG. 2 is a perspective view of a cartridge housing.

When a cartridge 200 is placed onto the elevator load arms 123, a linkage extending from the cam motor 110 mates with an external drive connector 240 extending from one side of the cartridge housing 210, shown in FIG. 2. Activation of the cam motor 110 initiates movement of the plate pairs of the cartridge, as will be more fully described below.

When vials are to be capped or de-capped, a vial tray 300 containing vials 310 is placed into the tray holder 180 when the conveyor slide 190 is at a left position. Once the vial tray 300 is loaded into the tray holder 180, the conveyor slide 190 moves the vial tray 300 into a cap/de-cap position under the elevator 120. The positioning of the tray should be carefully controlled and repeatable to ensure alignment of the cartridge with the vials. Alternatively, the vial trays 300 may be directly loaded/unloaded from the center position as well. If the vials 310 are being capped for the first time, the cartridge 200 will be pre-loaded with new caps. If the vials 310 are to be decapped, the cartridge 200 will be empty, ready to receive the caps that will be removed from the vials. The removed caps may either be discarded or retained on the cartridge for replacement on the vials when the desired operations are completed.

With the elevator 120 in a raised position, the cartridge 200 and vial trays 300 may be positioned for processing or removed after processing. A new cartridge is inserted between the elevator load arms 123. Both the new cartridge 200 and vial tray 300 may be identified with bar codes or alphanumeric characters. The system may include a bar code reader to confirm the correct pairing of tray and caps, or the bar codes may be scanned by a separate ID system prior to placement of the vial tray and/or cartridge into the system.

Once the cartridge 200 and vial tray 300 are loaded and aligned, the elevator 120 lowers to being the capping or de-capping process. Once the capping/de-capping operation is complete, the elevator 120 is moved to the raised position where the cartridge 200 and vial tray 300 may be removed.

If the caps are to be discarded, the conveyor slide 190 is activated to shift to the left so that a discharge chute 160 is positioned directly below the cartridge 200. The cam motor is activated to cause the cartridge to release the caps so that they drop into the discharge chute. The cam can be rotated a full 360° in the "reverse" direction in order to forcibly remove any sticky caps and ensure that no caps remain on the cartridge.

In an alternate embodiment, rather than moving the cassette down to the tray, the elevator is configured to lift the tray up toward the cassette, or two elevator mechanisms may be used so that both the cassette and the tray are vertically movable.

FIG. 2 illustrates a fully assembled cartridge 200 with cartridge housing 210. The sides of the cartridge along the long dimension of the housing have an opening therethrough at the center through which a cam race frame 273, 274 extends. Two smaller circular openings near the ends of each long side are formed to receive rods 252. On one side of the housing 210, an external drive connector 240 provides linkage between the cam shaft 263 (shown in FIG. 3) and the cam motor 110. In a preferred embodiment, an identification label 220 is disposed on one or more sides of housing 210 to permit identification of the cartridge 200 for matching up with a corresponding vial tray. The label 220 may be a bar code or alphanumeric code, which will be read by a conventional optical reader that can either be associated with, or separate from, the capper/de-capper system. Alternatively, RF-readable tags or readily legible characters, color coding or other visually distinguishable marking can be used to permit the user to identify the cartridge by sight for association with the appropriate vial tray.

Figure 3:
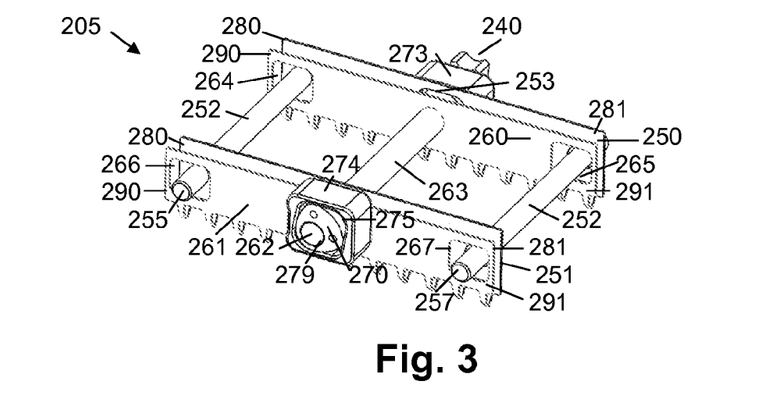
FIG. 3 is a perspective view of a first embodiment of the cartridge.
Figure 4A:
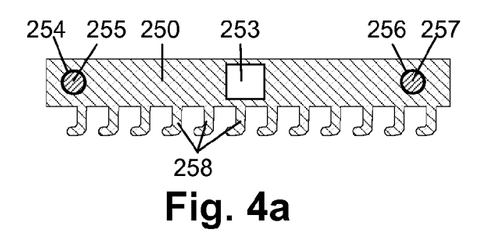
FIG. 4a is a side view of the static gripper plate.
Figure 4B:
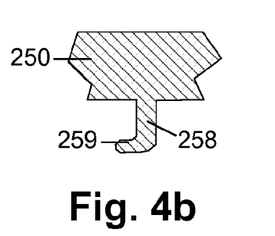
FIG. 4b is a detail view of the static gripper arm.
Figure 4C:
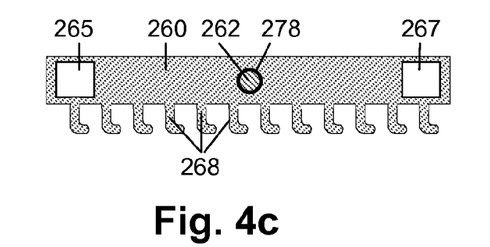
Figure 4D:
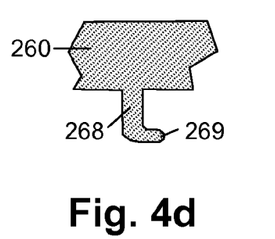
FIG. 4d is a detail view of the cam gripper arm.

The key components of the cartridge mechanism 205, illustrated without housing 210, are shown in FIG. 3. The cartridge mechanism 205 includes a plurality of sets of elongated gripper plates. A set of gripper plates consists of either two or three plates in which one plate is configured to remain stationary while the remaining one or two plates move relative to the stationary plate to modify width and angle of gripper arms extending from the plates. For ease of illustration, the exemplary embodiments are described as having a pair of plates, however, the construction and operation will not vary significantly when three plates are used.

In the exemplary embodiment, each plate pair consists of one static plate and one cam plate in each gripper plate pair. Each gripper plate has a plurality of gripper arms extending downward from the main body of the plate. The gripper arms are described in more detail below. In the illustrative embodiment, the arrangement is an 8×12 array with eight rows of paired gripper plates, each gripper plate having twelve gripper arms. In FIG. 3, for ease of illustration, only the first and eighth pairs of gripper plates for an 8×12 array are shown. The first pair of gripper plates includes the first static plate 250 and the first cam plate 260, while the eighth pair of gripper plates includes the second static plate 251 and the second cam plate 261. The cam plates abut and are slidable relative to their corresponding static plate.

In an alternate embodiment, the single opening in the lengthwise center of each plate is replaced with two or more openings that are aligned so that a cam shaft extends through each, each cam shaft having a pair of cams at its end. In this embodiment, the cooperation between the cam shaft openings of the two different plate types (cam plates and static plates) and the cam shaft remains the same as in the single cam shaft configuration described above, but has the added advantage that the force applied to the caps is more balanced.

The number of pairs of gripper plates depends upon the maximum quantity of vials and their arrangement of the vial tray. If a vial tray has a larger or smaller matrix, the number of plate pairs and lengths will vary accordingly.

Referring to FIGS. 3 and 4a-4d, each static plate 250, 251 has a first end 280 and a second end 281. A first opening 254 is formed through the static plate near the first end 280 and a second opening 256 is formed through the plate near the second end 281. A first static connecting rod 255 extends through the closely-fitted first opening 254 of each static plate and is fixedly retained at each end by openings formed in the cartridge housing 210 (shown in FIG. 2). A second static connecting rod 257 is passed through the second opening 257 of each static plate and is fixedly retained at each end within openings in the cartridge housing. A static plate spacer 252 is inserted over the static connecting rods between each adjacent plate pair, to maintain the spacing between the plate pairs. A third opening 253 is formed in each static plate 250, 251 midway along the length of the plate. This opening 253 is relatively large to permit the cam shaft 262 to move through its complete range of travel without contacting the inside edges of the opening. Opening 253 is generally square to accommodate the eccentric movement of the cam shaft.

Each cam plate 260, 261 has first end 290 and a second end 291. A circular opening 278 is formed towards the center of each cam plate. Each cam plate 260, 261 has a pair of square or rectangular openings 264-267 located near the ends of the plate. As illustrated, a first opening 264 is located near the first end 290 of the first cam plate 260 and a second opening 265 is located near the second end 291 of the second cam plate 261. A third opening 266 is located near the first end 290 of the second cam plate 261 and a fourth opening 267 is located near the second end 291 of the second cam plate 261. The static plate connecting rods 255, along with the static plate spacers 252, extend through these openings. The openings 264-267 are dimensioned to allow the cam plates 260, 261 to traverse their parallelogram path without binding against static connecting rods 255 (the static plate spacers 252), while serving as limits to the upper and lower extremes of travel of the cam plates 260, 261. The openings also assist in leveling the cam plates.

A cam shaft 262 extends through the circular opening 278 of each cam plate 260, 261 and into cam race frames 273, 274. Each cam plate is attached to the cam shaft 262 so that the cam shaft can rotate relative to the cam plates. A cam plate 270 is fixedly mounted on each end of the cam shaft by inserting the ends through a closely fitted opening 279 in the cam plate 270. An interference fit should hold the cam plates 270 firmly in place over the cam shaft ends, however, additional fastening means may be employed. A plurality of cam plate spacer sleeves 263, or similar spacer blocks, are fitted over the cam shaft 262 between each cam plate to maintain a constant spacing between adjacent plates.

Cam plate 270 has a generally triangular profile with the opening 279 located off center within the triangle. Each cam race 275 defines a parallelogram that is horizontal on the bottom and slightly skewed (approximately 10°) on the vertical. Referring to FIG. 3, the contact edges of the cam plate 270 interact with the cam race 275 within cam race frame 274, to affect an eccentric motion of the cam shaft 262 which simultaneously raises, shifts laterally, or lowers the cam plates relative to the static plates. The cam plate within cam race frame 273 is not visible in the figures, but mirrors the features and operation of cam plate 270 within cam race frame 274. The vertical skew of the cam races may be increased and/or the direction of the skew changed, as needed to accommodate different size vials and caps. Different size cartridges may be used in the system to accommodate different container sizes and counts, and different tray sizes, or to work with different or unusual brands of caps.

Gripper arms are formed on the bottom of each gripper plate for contacting and manipulating the vial caps. A plurality of static gripper arms 258 are formed on the bottom of the static plate 250 and a plurality of cam gripper arms 268 are formed on the bottom of cam plate 260. The static gripper arms 258 have profiles with hooked ends 259 that project in a direction opposite to the hooked ends 269 of the cam gripper arms 268. The hooked ends 259 of static gripper arms 258 are preferably somewhat rounded and have a relatively broad profile compared with the hooked ends 269 of the cam gripper arms, as can be seen in FIGS. 5b, 5f and 5h. The broader, more rounded profile on hooked ends 259 applies more uniform pressure to the cap recess during the skewing of the ends as shown in FIGS. 5e and 5f, and reduces the risk of rupturing the cap. One static gripper arm is paired with one (two, in the case of three plates) cam gripper arm(s) 268 to define a cap manipulator (258+268). One cap manipulator is provided for each potential vial location in the array. (Note that the present invention may be used to process a tray of vials that is less than full using the same cassette as is used for a full tray.) For the illustrative 8×12 array, there would be 12 cap manipulators on each pair of plates. The number of cap manipulators in a cartridge will vary depending on the vial array size, as will the dimensions and shape of the hooked ends 258, 269. For the 8×12 array described in the examples for use with caps currently commercially available, the range of travel of the cam plate(s) in both the horizontal and vertical directions is 6-7 mm, and more preferably in the range of 6.1 mm to 6.7 mm.

Figure 5A:
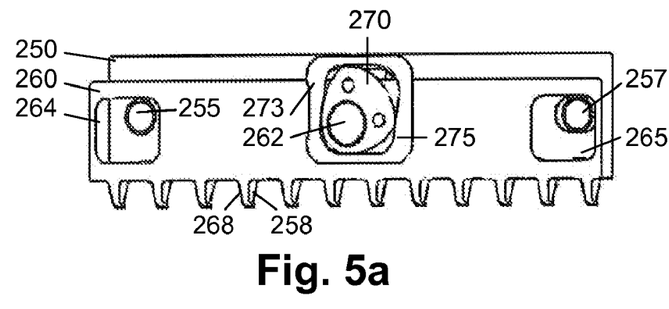
FIGS. 5a-5h are side and detail views of the gripper plates, gripper arms and cam according to the first embodiment illustrating the relative positions of the gripper plates, gripper arms, and cam for insertion into the cap recess (FIGS. 5a and 5b), gripping the cap (FIGS. 5c and 5d); lifting and stretching the cap (FIGS. 5e and 5f) and holding the cap (FIGS. 5g and 5h).
Figure 5B:
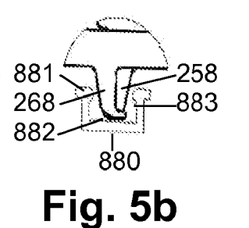
Figure 5C:
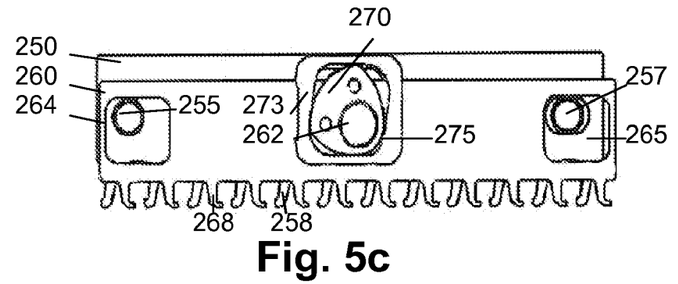
Figure 5D:
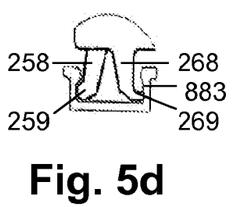
Figure 5E:
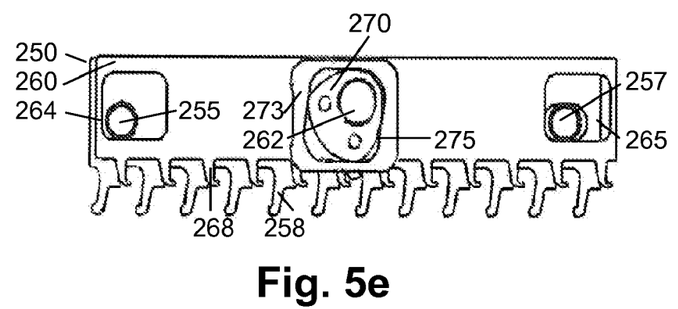
Figure 5F:
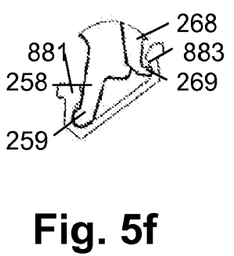
Figure 5G:
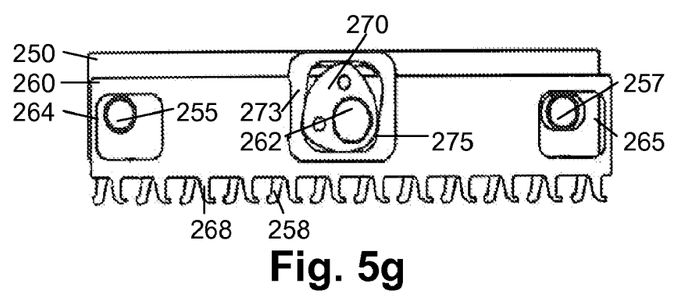
Figure 5H:
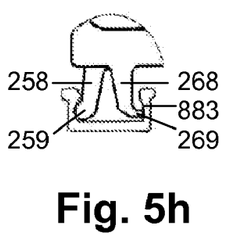

The operation of capping/de-capping mechanism of the first exemplary embodiment is illustrated in FIGS. 5*a*-5*h*. The vials are not shown. The first step is illustrated in FIGS. 5*a* and 5*b*, where the cam is in a first position and the gripper arms from each plate are in an overlapping alignment position. As the elevator 120 (FIG. 1) is lowered, each manipulator (258+268) is moved into a starting position within the top recess of cap 880. Alternatively, or in combination with the vertical movement of the cartridge, the tray full of vials, or a selected sub-set of vials, may be raised to engage the cartridge. In this way only the selected tubes will be de-capped. Because the static gripper arm 258 is overlapped with the cam gripper arm 268, the combined width is narrow and the gripper arms can be inserted into the cap recess without touching the recess sidewall 883. At its lowest extent, the manipulator may, but need not, contact the inner bottom surface 882 of cap 880.

As shown in FIG. 5*a*, the cam plate 260 is positioned downward and to the left relative to the cam plate 260. The static connecting rods 255 and 257 are disposed in the upper right hand corners of openings 264 and 265.

In the second step, illustrated in FIGS. 5*c* and 5*d*, the cam 270 and cam shaft 262 have been rotated counter-clockwise approximately 90°, causing the cam plate 260 to move to the right relative to the static plate 250. This movement causes the gripper arms to shift laterally, expanding the width of the manipulator (258+268) and causing it to contact the inner sidewall 883, with the hooked ends beneath cap lip 881.

At this point, the cam plate is downward and shifted to the right relative to the static plate 250. As seen in FIG. 5*c*, the static connecting rods 255, 257 are disposed in the upper left corners of openings 264 and 265.

The third step is illustrated in FIGS. 5*e* and 5*f*. The cam 270 continues to rotate in a counter-clockwise direction another approximately 90°. This rotation causes cam plate 260 to move upward relative to static plate 250, which has the effect of skewing the manipulator so that hook 269 catches the underside of lip 881 to apply an upward force to lift one side of the cap, stretching the cap between the hooks 259, 269 to break the seal between the cap and the inner surface of the top of the vial and remove the cap from the vial. In this position, the static connecting rods 255 and 257 are located in the lower left hand corner of opening 255 and 265. This step can be repeated some number of times to ensure that the caps are free from the vials. It can also be used in combination with motion of the conveyor to detect un-released caps or to further encourage the caps to dislodge from the vials.

The fourth step is illustrated in FIGS. 5*g* and 5*h*. The elevator 120 is activated to lift the cartridge 200, and the caps retained on the manipulators, away from the vials. While the elevator is raised, the cam 270 and cam shaft 262 are rotated clockwise 90° to return the cam plates to the same relative position shown in FIGS. 5*c* and 5*d*, with the hooks 259, 269 spread apart at a distance to apply sufficient pressure to inner sidewalls 883 to retain the caps 880 on the manipulators. At this point, the cartridge and the de-capped vial tray may now be removed from the capper/de-capper.

The dimensions of cartridge housing 210 are preferably selected so that caps retained on the gripper arms are withdrawn safely above the lower edge of the housing. A removable protective cover can be placed across the open bottom of the cartridge to prevent contamination of the caps until the user is ready to replace the caps on the vials. The cartridge is preferably configured so as to allow multiple cartridges to be stacked and/or to be handled robotically.

For inserting caps into vials in a tray, the sequence described above will be reversed.

Figure 6:
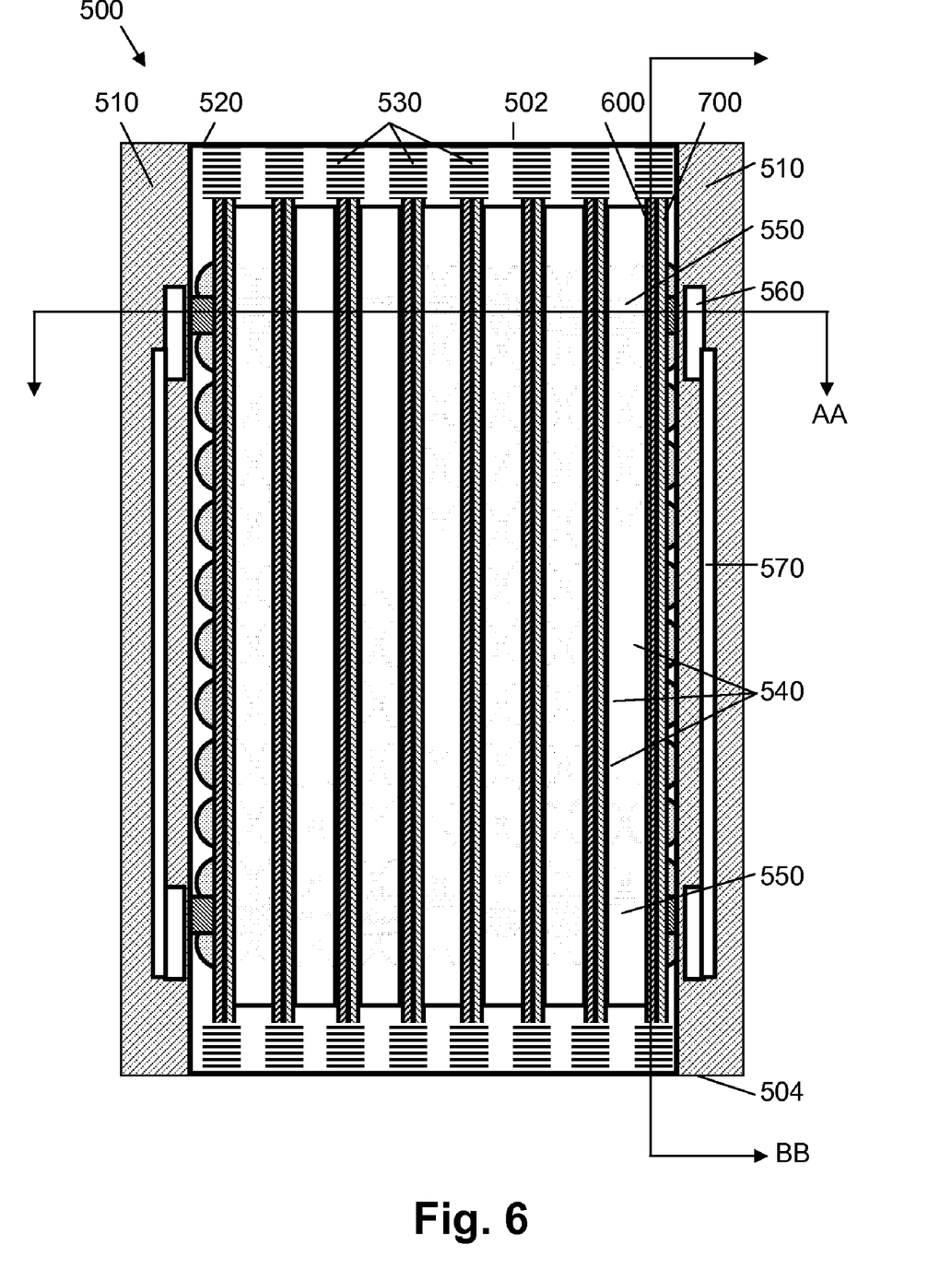
FIG. 6 is a top view of a second embodiment of the cartridge.

FIGS. 6-9 illustrate a second embodiment of the cartridge for use in the inventive system for simultaneous removal or replacement of a plurality of caps 540 from an array of vials. FIG. 6 provides a top view of the second embodiment of the cartridge 500 comprising a support frame 510, a plurality of paired gripper plates 600,700, a pair of springs 530 for each gripper plate pair, two rectangular cam rods 580, two pivot arms for each cam rod 560, and two cam linkages 570. The caps 540 are diagrammatically shown in FIG. 6 for reference. Cartridge 500 preferably includes a protective housing (not shown) which encloses the various components.

The 96 cap array shown in FIG. 6 has 8 caps to a row and 12 caps to each column. As illustrated, the overall dimensions of the cartridge 500 are selected to match the dimensions of the vial array. For capping and de-capping vials in such a 96 vial tray, there will be 8 gripper plate pairs, each having 12 gripper arms, all spaced to match the vial spacing in the tray. The quantity and distribution of vials in the tray are intended to be exemplary only. As will be readily apparent, different numbers of gripper plate pairs and gripper arms may be used for different tray sizes and vial quantities.

In FIG. 6, the top edge of each gripper plate pair 600, 700 is visible, while FIG. 2*a* provides an end view of each gripper plate. Each pair of gripper plates 600, 700 comprises a first gripper plate 600 and a second gripper plate 700, which are shown separated in FIGS. 8*a* and 8*b*. Each gripper plate has a plurality of gripper arms and a pair of cam openings near the ends of the plate. The first gripper plate 600 and the second gripper plate 700 in each pair of gripper plates are retained within the support frame 510 in slidable contact with each other. The pairs of gripper plates are spaced at uniform distances, with the distance corresponding to the distance between the center to center distances of the vials in the tray. In the preferred embodiment, plate spacers 550 are inserted over the cam rod 380 and between adjacent plate pairs to maintain proper spacing. A spring is disposed between the end of each pair of gripper plates and the support frame to bias the gripper plates toward the center of the cartridge.

A pair of cam rods is used to actuate the gripper plates. FIG. 8*c* shows a cross-sectional view of a cam rod 580 with a first radius, a second radius, a major diameter corresponding to the greatest distance between the two radii and a minor diameter corresponding to the narrowest portion of the cross-section. The cam rod 580 has a length that extends through all gripper plates in the cartridge to effect movement of all gripper plate pairs simultaneously. The ends of each cam rod extend through an opening in the side of the support frame 510 where each end is connected to a pivot arm 560. The cam rods 580 are rotatably supported within the opening in the support frame 510 so that they may be rotated to effect relative movement of the gripper plate pairs.

A pivot arm 560 is attached at its lower end to each end of the cam rods 580, creating a fixed pivot point. The upper ends of the pivot arms 560 on each side of the cartridge are pivotably attached to a connecting bar 570 by an upper pivot rod 595 disposed above the support frame, parallel to the cam rod 580. The combination of the pivot arms 560, the two upper pivot rods 595 and the two connecting bars 570 form a control frame that effects simultaneous rotation of all cam rods 580 when the control frame is moved in a direction parallel to the sides of the cartridge.

When placed in the cartridge holder of the capper/de-capper system, such as the one shown in FIGS. 1a and 1b, the control frame is linked to a drive means that moves in a direction parallel to the sides of the cartridge. In other words, the cam motor for the second embodiment would move laterally rather than rotating as in the first embodiment.

Figure 7A:
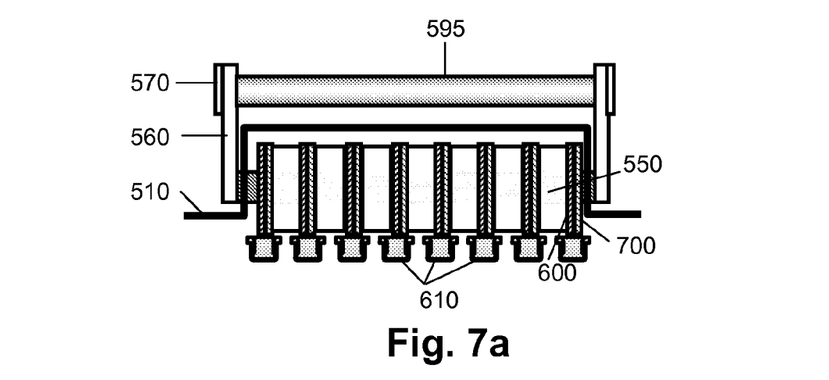
FIGS. 7a and 7b are cross-sectional views taken along lines AA and BB, respectively, of FIG. 6.
Figure 7B:
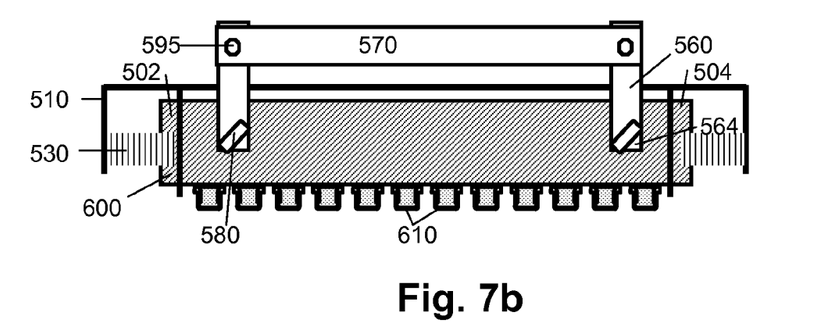

FIG. 7b shows the cam rods 580 and control frame elements at the home position with the gripper arms aligned with and inserted into the caps, but not gripping the caps. In the home position, the pivot arms 560 are perpendicular to the rectangular connecting bars 570, the gripper plates, and the horizontal plane of the support frame 510.

Figure 8A:
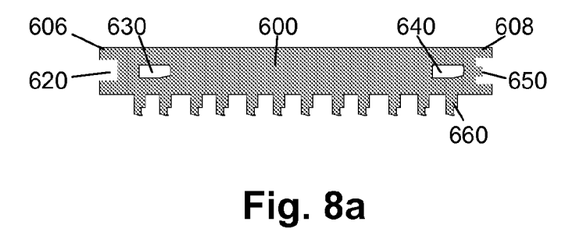
FIG. 8a is a side view of a first gripper plate.
Figures 8B, 8C:
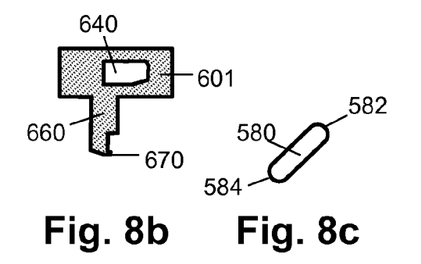
FIG. 8b is a detail view of a first gripper arm.
FIG. 8c is an end view of a cam.

FIGS. 8a and 8b illustrate a pair of gripper plates comprising a first plate 600 and a second plate 700, each gripper plate having a plurality of gripper arms extending from its lower edge. The gripper plates are slidably supported in the support frame so that the gripper arms extend downward with respect to the horizontal plane of the cartridge. The gripper plates are preferably made from stainless steel, but may be made from rigid durable plastic or polymer, or other appropriate material.

Figures 8D, 8E:
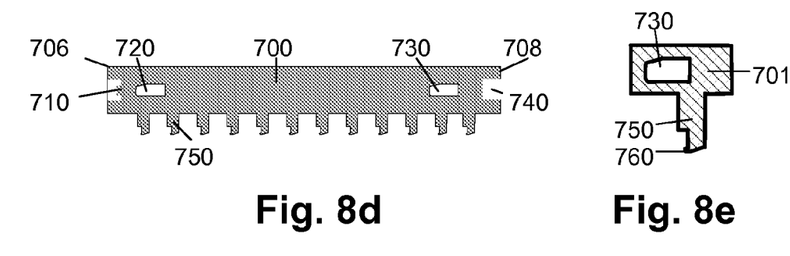
FIG. 8d is a side view of a second gripper plate.
FIG. 8e is a detail view of a second gripper arm.

Each end of the first plate 600 has a rectangular notch 620 formed therein. The notch on the second end 608 has a small protrusion 650 at its center to assist in centering of the spring 530. The second plate 700 has similar notches 740 formed therein with the relative positions reversed, so that the spring-centering protrusion 710 is on the first end.

Referring to FIGS. 6 and 7b, a plurality of springs 530 are attached to the first end 502 and second end 504 of the vertical frame surface 520 so that one spring extends between one end of a pair of gripper plates and the vertical frame surface 520. The springs 530 is held in contact with the gripper plates by the end notches 650 and 510. The springs 530 bias the first and second gripper plates in opposing directions so that they remain in contact with the cam 580. As the cam 580 rotates, the first plates 600 move horizontally towards the first end 502 of the cartridge 500 and the plurality of second plates 700 to move horizontally towards the second end 504 of the cartridge.

Each plate has at least two cam openings 630, 640 and 720, 730 formed therein for receiving the corresponding cam rod 580. Each cam opening is generally rectangular with an angled corner for interacting with one of the first radius and second radius of the cam 580 to effect relative movement of the plates. The positions of the angled corners will be diametrically opposite each other. For example, as illustrated in FIGS. 8b and 8e, the cam opening 640 in the first plate 600 is angled on the lower right corner, while the cam opening 730 in the second plate is angled on the upper left corner.

The edges of the cam openings in the gripper plates form a race for interacting with the cam bars 580. On the first gripper plate, a first race is defined by cam opening 630 and a second race is defined by cam opening 640. On the second gripper plate, the first race is defined by cam opening 720 and the second race is defined by cam opening 730. As the cam rotates, the gripper plates move in an up, down, left, or right direction in response to interaction between the cam and the races.

Referring to FIGS. 8b and 8e, the upper portion of a gripper arm 660, 750 of the gripper plates 600 and 700, respectively, is rectangular in shape and of sufficient width to prevent entry of the upper portion into the cap recess. To facilitate illustration of the interaction between the cam and gripper plates, a single gripper is shown in FIGS. 8b and 8e and FIGS. 9a-9e, with each having a corresponding cam opening. Typically, there will be two or more cam openings for a larger plurality of gripper arms. For example, as illustrated in FIGS. 8a and 8d, there are two cam openings 630 and 640 shown in the first plate and two openings 720 and 730 in the second plate, while each plate has 12 gripper arms.

The lower portion of each gripper arm includes an outward-facing hook 670, 760 at the distal end. The width of the gripper arm 660, 750 is stepped, so that a shoulder is formed at a distance above the hook that generally corresponds to the depth of the cap recess, allowing the hook portion to extend into the cap recess with the shoulder at the top of the recess. As is apparent from FIGS. 9b-9e, the hook of each gripper arm generally conforms to the side profile of the cap recess so that when the two gripper arms are positioned for operation, the combined shape of the hook portions and shoulder lip portions of the two gripper arms generally matches the profile of the cap recess. During operation of the capper/de-capper, the shoulder contacts and, when needed, presses down on the upper edge of the cap, as will be described below with regard to FIGS. 9a-9e.

Figure 9A:
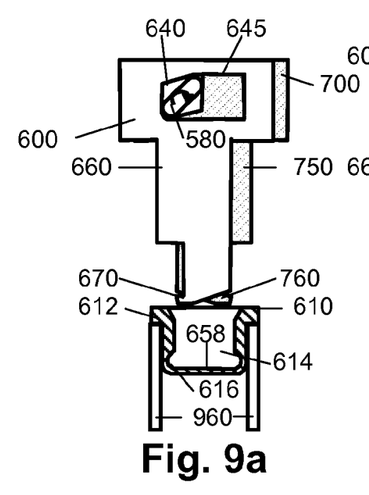
FIGS. 9a-9e are side views of gripper arms and cam according to the second embodiment during operation of the cartridge for: centering of the cap recess (FIG. 9a), insertion into the cap recess (FIG. 9b), gripping the cap (FIG. 9c), stretching the cap (FIG. 6d), and lifting the cap (FIG. 6e).

FIGS. 9a-e illustrate the relative gripper arm movements with rotation of the cam 580. FIG. 9a illustrates the first step where the mechanism is at the home position. The bias provided by the springs causes the horizontal width of the cam openings to be minimized. In this home position, the radii of the cam 580 are oriented to coincide with the square corners of the cam openings of the two plates. At this point, the upper edges of the plates are even and parallel. The first radius of the cam 580 is in contact with the lower left corner of the cam opening 640 of the first plate 600 and the second radius of cam 580 is in contact with the upper right corner the cam opening 640 of the second plate 700. The two radii are in continual contact with the cam race 645. The gripper arms are above the cap 610 and the first gripper arm 660 and the second gripper arm 750 overlap each other such that no part of the gripper arms will touch the cap 610 when inserted into the cap 610, which is in the top of the vial 960.

Figures 9B, 9C:
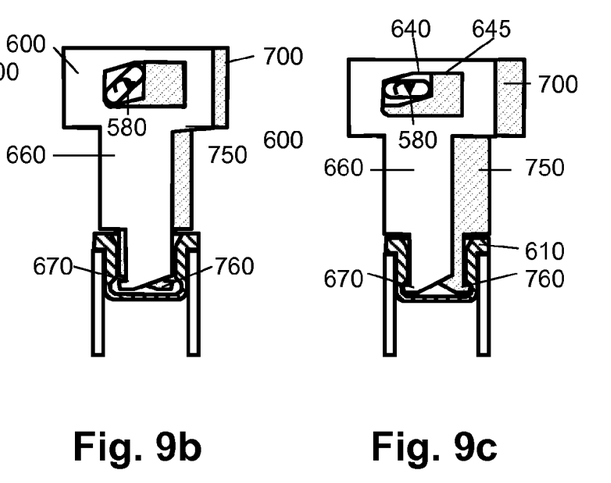

FIG. 9b illustrates the second step of the mechanism where the elevator, not shown, lowers the cartridge so that the gripper arms are inserted into the cap's hollow interior 614. At this point, no part of the gripper arms contact the caps 610. Although it is not shown, the pivot arms will be perpendicular to the rectangular connecting bars, the gripper plates, and the horizontal plane of the frame. The rectangular connecting bars are parallel to the gripper plates.

FIG. 9c illustrates the third step where the cam 580 is rotated clockwise to a horizontal position and the cam's width causes first gripper plate 600 and the second gripper plate 700 to move apart in opposite horizontal directions forcing the horizontal width of the combined cam openings to expand, but the top edges of the plates still even. This movement causes the combined widths of the lower portions of the gripping arm to expand to the inner diameter of the cap recess, with the outside edges of the hooks to come into contact with the cap indent 616. The cam drive motor, not shown in the apparatus is operationally connected to the rectangular connecting bar of the cartridge and pulls the rectangular connecting bar in a horizontal motion causing the cam to rotate within the cartridge. The springs at the ends of the gripper plates cause the cam openings within the gripper plates to be biased against the cam.

Figure 9D:
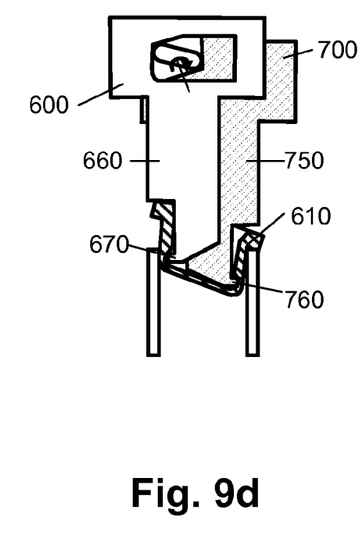

FIG. 9d illustrates the fourth step where the cam 580 continues to be rotated clockwise. The first radius of the cam 580 contacts the left upper angled corner of the cam opening in the first plate 600 and the right lower angled corner of the cam opening in the second plate 700. This causes the first plate 600 to move vertically upward relative to the second plate 700, lifting the left side of the cap. The second gripper plate 700 remains in the same position as in the previous step. The vertical motion of the first plate raises one edge of the cap 610. The angled orientation of the cap stretches it, breaking the seal between the outer diameter of the cap and the inner diameter of the vial 960. With the force between the cap and the vial released or significantly reduced, the cap can be easily separated from the vial. As will be readily apparent to those of skill in the art, the plates may be interchangeable such that the second plate lifts while the first plate remains vertically fixed.

Figure 9E:
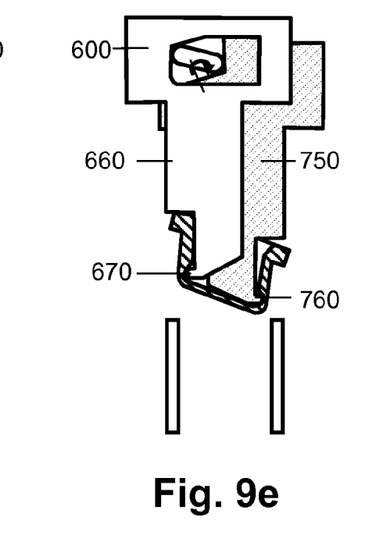

FIG. 9e illustrates the fifth step during which the elevator is activated to lift the cartridge away from the vials. The cartridge may now be removed from the system. The contents of the vials are ready for analysis or further processing and the tray may now also be removed.

To prevent cross-contamination, each tray will have an orientation indicator and a unique identifier to ensure that the correct caps are associated with the vials. When the cartridge with the removed caps is removed from the apparatus, the exposed surface can be covered with a lower protective cover so the cartridge can be stored and stacked. The cartridge is identified such that the tray and cartridge can be matched up again for the re-capping process, which can be performed using the system operated according to the above sequence in reverse, with the cam rotated in a counter-clockwise direction. Additional features can be added to the spacer blocks 550 to assist in seating the caps during the re-capping process. The cams may be further rotated in the counter clockwise direction to ensure that no caps remain stuck to the cartridge.

Other embodiments and modifications of the present invention will occur readily to those of ordinary skill in the art in view of these teachings. Therefore, this invention is to be limited only by the following claims which include all such other embodiments and modifications when viewed in conjunction with the foregoing specification and accompanying drawings.

What is claimed is:

1. A device for alternatively simultaneously removing caps from and simultaneously replacing caps into a plurality of containers disposed within an array having a plurality of rows and a plurality of columns, wherein each cap has a recessed top, the device comprising:
   a cartridge comprising:
   a frame;
   a plurality of sets of gripper plates disposed within the frame, with one set of gripper plates corresponding to each column of the array, wherein each gripper plate comprises a plurality of gripper arms extending downward relative to the frame, with one gripper arm corresponding to each row of the array, wherein each gripper arm has a hooked end extending in a plane of the gripper plate and the hooked ends of all gripper arms on a gripper plate extend in one direction, and wherein the hooked ends of one gripper plate of each set of plates extend in an opposite direction from the hooked ends of another gripper plate of the set, wherein each plate has a corresponding gripper arm on the other gripper plate so that a pair of gripper arms defines a manipulator; and
   a rotating cam assembly having a cam shaft for cooperating with the gripper plates to change a relative position of one gripper arm relative to its corresponding gripper arm so that the manipulator engages an indent of a hollow portion of the cap and expands, skews and contracts to grip, stretch, and release the cap, respectively; and
   a drive means for rotating the cam assembly.

2. The device of claim 1, wherein the frame and plurality of sets of gripper plates are separable from the drive means.

3. The device of claim 1, wherein the at least one cam assembly further comprises a cam plate disposed near each end of a cam shaft and a cam race for defining a parallelogram path described by each cam plate.

4. The device of claim 1, wherein each set of gripper plates comprises a static plate and a cam plate.

5. The device of claim 4, wherein each static plate of the plurality of sets is attached to a static locating rod which is attached to the frame.

6. The device of claim 4, wherein each set of gripper plates is separated by spacers.

7. The device of claim 4, further comprising:
   a conveyor for transporting a tray of containers from a loading position to a position aligned with the cartridge; and
   an elevator for moving one of the cartridge and the tray vertically relative to the other.

8. The device of claim 7, further comprising a discard bin disposed on the conveyor for receiving caps released by the cartridge.

9. The device of claim 4, further comprising a removable cover for protecting caps retained on the cartridge.

10. A device for alternatively simultaneously removing caps from and simultaneously replacing caps into a plurality of containers disposed within an array having a plurality of rows and a plurality of columns, wherein each cap has a recessed top, the device comprising:
    a cartridge comprising:
    a frame;
    a plurality of sets of gripper plates disposed within the frame, with one set of gripper plates corresponding to each column of the array, wherein each gripper plate comprises an elongated body with a plurality of gripper arms extending downward therefrom, with one gripper arm corresponding to each row of the array, wherein each gripper arm has a hooked end extending in a plane of the gripper plate and the hooked ends of all gripper arms on a gripper plate extend in one direction, and wherein the hooked ends of one gripper plate of each set of plates extend in an opposite direction from the hooked ends of another gripper plate of the set, wherein each gripper arm on one gripper plate of a set cooperates with a corresponding gripper arm on another gripper plate of the set to define a manipulator; and
    at least one cam assembly having a shaft portion that extends through a plurality of openings in each set of gripper plates, wherein rotation of the cam assembly induces relative motion between gripper plates of each set of gripper plates, causing each manipulator to undergo a sequence of shape changes, wherein the sequence of shape changes includes the steps of expanding a width of the manipulator to grip an indent of a hollow portion of the cap, skewing the manipulator to stretch the cap at an angle, and contracting to release the cap; and
    a drive means for rotating the cam assembly.

11. The device of claim 10, wherein the frame and plurality of sets of gripper plates are separable from the drive means.

12. The device of claim 11, further comprising a removable cover for protecting caps retained on the cartridge.

13. The device of claim 10, wherein the at least one cam assembly further comprises a cam plate disposed near each end of a cam shaft and a cam race for defining a parallelogram path described by each cam plate.

14. The device of claim 10, wherein each set of gripper plates comprises a static plate and a cam plate.

15. The device of claim 14, wherein each static plate of the plurality of sets is attached to a static locating rod which is attached to the frame.

16. The device of claim 10, wherein each set of gripper plates is separated by spacers.

17. The device of claim 10, further comprising:
 a conveyor for transporting a tray of containers from a loading position to a position aligned with the cartridge; and
 an elevator for moving one of the cartridge and the tray vertically relative to the other.

18. The device of claim 17, further comprising a discard bin disposed on the conveyor for receiving caps released by the cartridge.

* * * * *